US007396526B1

(12) United States Patent
Cole et al.

(10) Patent No.: US 7,396,526 B1
(45) Date of Patent: *Jul. 8, 2008

(54) SKIN CARE COMPOSITION

(75) Inventors: Curtis A. Cole, Langhorne, PA (US); Laura E. Flack, Birmingham, AL (US); Claudia Kaminski, Milford, NJ (US); Victoria Van Leeuwen, Le Vaudreuil (FR); Elvin R. Lukenbach, Flemington, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/565,716

(22) Filed: May 5, 2000

Related U.S. Application Data

(63) Continuation-in-part of application No. 09/436,867, filed on Nov. 9, 1999, now Pat. No. 6,544,531.

(60) Provisional application No. 60/107,956, filed on Nov. 12, 1998.

(51) Int. Cl.
*A61K 31/74* (2006.01)
*A61K 9/00* (2006.01)
*A61K 8/02* (2006.01)

(52) U.S. Cl. .............. 424/78.03; 424/400; 424/401

(58) Field of Classification Search ............. 424/400, 424/401, 78.03; 514/557, 558, 559, 667, 514/703
See application file for complete search history.

(56) References Cited

U.S. PATENT DOCUMENTS

| 3,205,135 A | 9/1965 | Tybring |
| 3,551,554 A | 12/1970 | Herschler |
| 3,875,198 A | 4/1975 | Strobel |
| 3,878,229 A | 4/1975 | Strobel |
| 4,021,572 A | 5/1977 | Van Scott et al. |
| 4,105,782 A | 8/1978 | Yu et al. |
| 4,197,316 A | 4/1980 | Yu et al. |
| 4,199,562 A | 4/1980 | Vanlerberghe et al. |
| 4,224,339 A | 9/1980 | Van Scott et al. |
| 4,234,599 A | 11/1980 | Van Scott et al. |
| 4,283,386 A | 8/1981 | Van Scott et al. |
| 4,380,549 A | 4/1983 | Van Scott et al. |
| 4,491,534 A | 1/1985 | Vanlerberghe et al. |
| 4,505,896 A | 3/1985 | Bernstein |
| 4,620,037 A | 10/1986 | Vanlerberghe et al. |
| 4,888,437 A | 12/1989 | Zeidler et al. |
| 4,971,789 A | 11/1990 | Vanlerberghe et al. |
| 5,152,419 A | 10/1992 | Yanagi |
| 5,204,105 A | 4/1993 | Mausner |
| 5,352,389 A | 10/1994 | Gazzani |
| 5,470,884 A | 11/1995 | Corless et al. |
| 5,523,090 A | 6/1996 | Znaiden et al. |
| 5,554,647 A | 9/1996 | Perricone |
| 5,574,063 A | 11/1996 | Perricone |
| 5,607,691 A | 3/1997 | Hale et al. |
| 5,626,856 A | 5/1997 | Berndt |
| 5,635,469 A | 6/1997 | Fowler et al. |
| 5,643,586 A * | 7/1997 | Perricone .................. 424/401 |
| 5,646,186 A | 7/1997 | Wang et al. |
| 5,665,776 A | 9/1997 | Yu et al. |
| 5,679,374 A | 10/1997 | Fanchon et al. |
| 5,744,148 A * | 4/1998 | Habif et al. .................. 424/401 |
| 5,747,049 A | 5/1998 | Tominaga |
| 5,753,637 A | 5/1998 | Fried |
| 5,847,003 A | 12/1998 | Ptchelintsev et al. |
| 5,856,357 A | 1/1999 | Yu et al. |
| 5,879,690 A | 3/1999 | Perricone |
| 5,889,054 A | 3/1999 | Yu et al. |
| 5,922,346 A | 7/1999 | Hersh |
| 5,932,229 A | 8/1999 | Ptchelintsev et al. |
| 5,942,250 A | 8/1999 | Yu et al. |
| 5,968,532 A | 10/1999 | De Lacharriere et al. |
| 5,972,993 A | 10/1999 | Ptchelintsev |
| 5,994,330 A | 11/1999 | El Khoury |
| 6,015,575 A | 1/2000 | Luther et al. |
| 6,017,556 A | 1/2000 | Luther et al. |
| 6,068,847 A | 5/2000 | Aleles et al. |

(Continued)

FOREIGN PATENT DOCUMENTS

DE          2436467 A          2/1976

(Continued)

OTHER PUBLICATIONS

PCT International Search Report dated Feb. 7, 2000.

(Continued)

*Primary Examiner*—Alton Pryor

(57) ABSTRACT

There are provided compositions which include a retinoid and preferably retinal; a dermatologically active acid; and a volatile base, such as ammonium hydroxide. Another embodiment of the invention includes compositions comprising a retinoid and preferably retinal; a dermatologically active acid; a volatile base; and a second neutralizing agent. There are also provided compositions which include a retinoid, a neutralized ammonium salt of a dermatologically active acid, and optionally a neutralized salt, other than ammonium salt, of an acid. Further provided are methods for reducing fine lines, wrinkles, skin roughness, and pore size and for increasing the clarity of a skin surface, cellular turnover, skin radiance, skin smoothness, skin permeation or collagen synthesis in a mammal in need thereof. Compositions as described above are administered topically to the skin of the animal.

22 Claims, 4 Drawing Sheets

U.S. PATENT DOCUMENTS

| | | | |
|---|---|---|---|
| 6,069,169 | A | 5/2000 | Ptchelintsev et al. |
| 6,120,779 | A | 9/2000 | Nayak et al. |
| 6,162,419 | A | 12/2000 | Perricone et al. |
| 6,180,133 | B1 | 1/2001 | Quan et al. |
| 6,183,747 | B1 | 2/2001 | Ren |
| 6,265,364 | B1 | 7/2001 | Kilpatrick-Liverman et al. |
| 6,277,881 | B1 | 8/2001 | Santhanam et al. |
| 6,319,942 | B1 | 11/2001 | Perricone |
| 6,333,356 | B1 | 12/2001 | Ptchelintsev et al. |
| 6,365,623 | B1 | 4/2002 | Perricone |
| 6,607,735 | B2 | 8/2003 | Cole et al. |
| 2002/0071818 | A1 | 6/2002 | Cole et al. |
| 2003/0095991 | A1 | 5/2003 | Cole et al. |
| 2004/0191206 | A1 | 9/2004 | Cole et al. |
| 2004/0213754 | A1 | 10/2004 | Cole et al. |
| 2005/0238730 | A1 | 10/2005 | Le Fur et al. |

FOREIGN PATENT DOCUMENTS

| | | | |
|---|---|---|---|
| DE | 4323174 | C2 | 7/1993 |
| EP | 029000 | | 5/1981 |
| EP | 0109102 | A2 | 5/1984 |
| EP | 0109103 | | 5/1984 |
| EP | 0158090 | B1 | 8/1990 |
| EP | 0396857 | A1 | 11/1990 |
| EP | 0413528 | B1 | 2/1991 |
| EP | 0343694 | B1 | 11/1992 |
| EP | 0530865 | A | 3/1993 |
| EP | 0649834 | A1 | 4/1995 |
| EP | 0852949 | A2 | 7/1998 |
| EP | 0 858 799 | A2 | 8/1998 |
| EP | 1090630 | A1 | 4/2001 |
| EP | 1192939 | A2 | 4/2002 |
| EP | 1219288 | A2 | 7/2002 |
| FR | 2504530 | A1 | 4/1981 |
| FR | 2604625 | A1 | 10/1986 |
| FR | 2648132 | A1 | 6/1989 |
| FR | 2742990 | A1 | 12/1995 |
| GB | 474820 | | 4/1935 |
| GB | 1050756 | | 9/1965 |
| GB | 1182320 | | 2/1970 |
| GB | 1589224 | | 5/1981 |
| JP | 06009517 | A2 | 1/1985 |
| JP | 4-95008 | A | 3/1992 |
| JP | 05058971 | A2 | 3/1993 |
| JP | 06145134 | A2 | 5/1994 |
| JP | 06247826 | A2 | 9/1994 |
| JP | 07223920 | A2 | 8/1995 |
| JP | 11071233 | A1 | 3/1999 |
| WO | WO98/00505 | A | 1/1998 |
| WO | WO98/04280 | | 2/1998 |
| WO | WO98/23152 | A | 6/1998 |
| WO | WO98/40063 | | 9/1998 |
| WO | WO99/06431 | A1 | 2/1999 |
| WO | WO99/06437 | A1 | 2/1999 |
| WO | WO99/45900 | A1 | 9/1999 |
| WO | WO99/45922 | A1 | 9/1999 |
| WO | WO00/01351 | A1 | 1/2000 |
| WO | WO00/16739 | A | 3/2000 |
| WO | WO00/27353 | A1 | 5/2000 |
| WO | WO01/01949 | A | 1/2001 |
| WO | WO01/49250 | A2 | 7/2001 |

OTHER PUBLICATIONS

Neutrogena Pore Refining Cream, 1 oz. size product packaging, launched May 11, 1999.

Neutrogena Pore Refining Cream, SPF 15, 1 oz. size product packaging, launched Feb. 28, 2000.

Neutrogena Skin Clearing Moisturizer, 1 oz. size, product packaging, launched Feb. 28, 2000.

Pending U.S. Appl. No. 09/436,867, Johnson & Johnson Consumer Companies, Inc.

Pending U.S. Appl. No. 09/325,452, Johnson & Johnson Consumer Companies, Inc.

PCT Search Report dated Jan. 2, 2002 of International Application No. PCT/US01/14533.

Supplementary European Search Report dated May 13, 2004, for corresponding EP application 99961660.0.

Database Caplus Online Chemical Abstracts Service, Columbus, Ohio, US, retrieved from STN Database accession No. 1993:415138 XP002226432 abstract & SU 1 738 081 A(USSR) May 30, 1992.

U.S. Appl. No. 09/677,738, filed Oct. 2, 2000—abandoned Mar. 13, 2006, Johnson & Johnson Consumer Companies, Inc.

U.S. Appl. No. 09/677,737, filed Oct. 2, 2000, Johnson & Johnson Consumer Companies, Inc.

U.S. Appl. No. 60/237,230, filed Oct. 2, 2000, Johnson & Johnson Consumer Companies, Inc.

U.S. Appl. No. 10/435,768, filed May 12, 2003—abandoned Jun. 9, 2005, Johnson & Johnson Consumer Companies, Inc.

International Search Report PCT/US01/14533 dated Jan. 2, 2002.

EPO Search Report EP 01308360 dated Jan. 9, 2002.

EPO Search Report EP 02256577 dated Jan. 22, 2003.

International Search Report PCT/EP 02/13009 dated Apr. 1, 2003.

EPO Search Report EP 01310844 dated Jun. 4, 2003.

EPO Search Report EP 01308359 dated Sep. 3, 2004.

Chinese Notice of Office Action dated Nov. 26, 2004 for Appln. No. 01143646.8.

Partial European Search Report EP 05 25 0363 dated May 11, 2005.

* cited by examiner

SKIN CARE COMPOSITION

This application is a continuation-in-part of U.S. Ser. No. 09/436,867, filed Nov. 9, 1999, now U.S. Pat. No. 6,544,531, which is a continuation-in-part of U.S. Ser. No. 09/325,452, filed Jun. 3, 1999, now U.S. Pat. No. 6,521,237, which claims priority from U.S. Ser. No. 60/107,956, filed Nov. 12, 1998, all of which are herein incorporated by reference.

FIELD OF THE INVENTION

This invention relates to skin care compositions which include, in a single formulation, the beneficial ingredients for aging or photodamaged skin, retinol and an acid.

BACKGROUND OF THE INVENTION

Retinol or vitamin A alcohol is useful in the reduction of fine lines, wrinkles, and mottled hyperpigmentation in skin. Hydroxy acids, and particularly alpha-hydroxy acids, are useful in increasing the clarity of the skin surface, increasing cellular turnover, and increasing skin radiance and smoothness. Ascorbic acid has skin permeation and collagen synthesis activity.

Retinol is physically unstable and rapidly degrades when stored at a pH below about 5. Acids such as hydroxy acids, and particularly alpha-hydroxy acids and ascorbic acid, on the other hand, are not active in increasing skin cell turnover, exfoliation, skin permeation, and/or collagen synthesis at pHs above about 5.

Consequently, retinol and hydroxy acids and/or ascorbic acid have generally been packaged separately. Retinol typically is packaged in a vehicle at a pH above about 5, while alpha-hydroxy acids and ascorbic acid are packaged at a pH of about 4 or below. Therefore, one must apply two separate products in order to achieve the benefit of both of these ingredients.

The present inventors have discovered a single composition which include both of these ingredients, in which both of these ingredients are stable, and in which both of these ingredients are active upon application to the skin.

SUMMARY OF THE INVENTION

Figure 1:
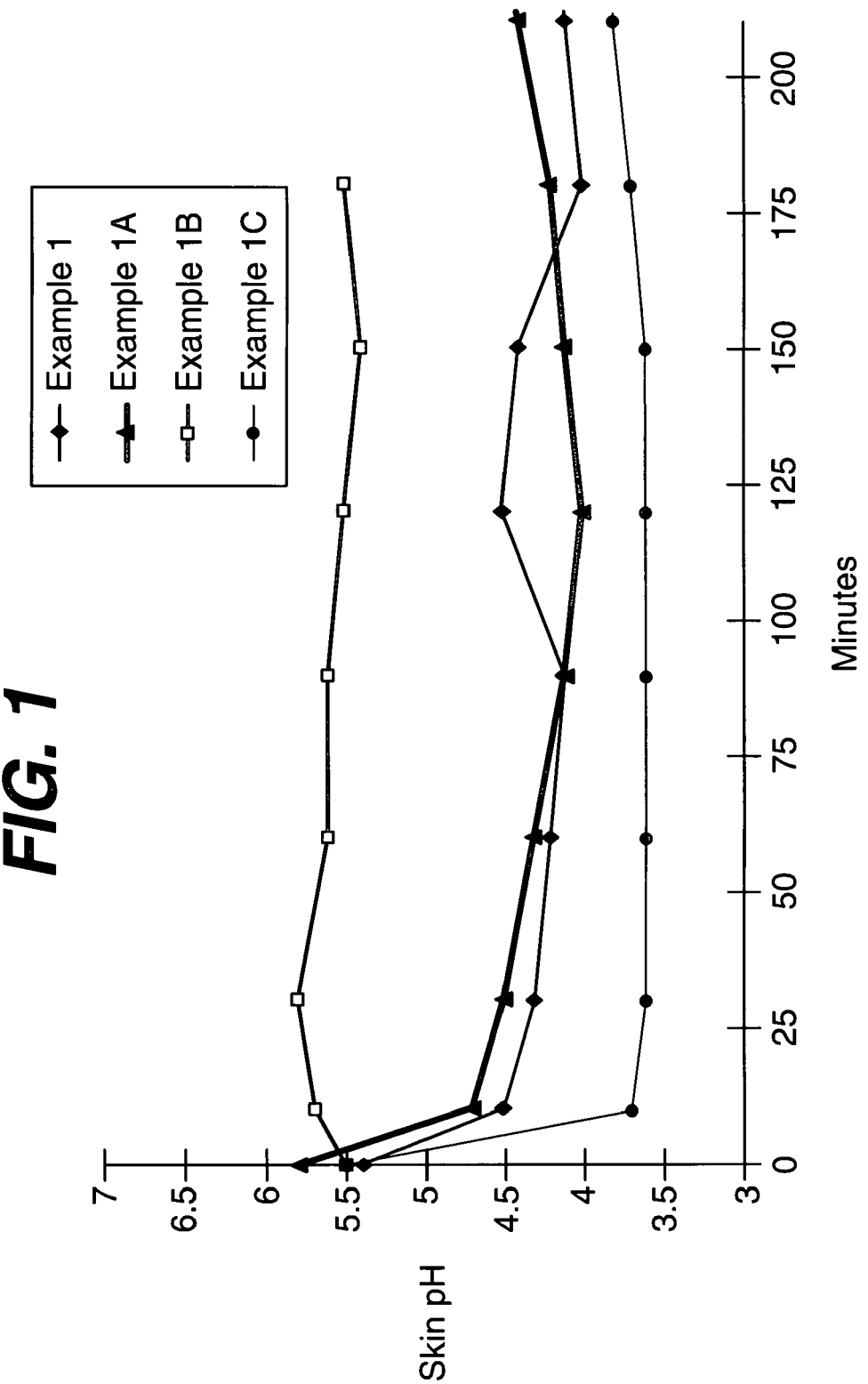
FIG. 1 is a graphic illustration of skin pH over time after treatment.

According to one embodiment of the present invention there are provided compositions which include:
(A) a retinoid and preferably retinol;
(B) a dermatologically active acid; and
(C) a volatile base, such as, for example, a volatile compound comprising an amine such as ammonium hydroxide or 2-dimethylaminoethanol (N,N-dimethylethanolkamine or DMAE). Volatile bases have a vapor pressure typically below atmospheric pressure, preferably below about 700 mm Hg, and more preferably below about 600 mm Hg. The volatile base preferably evaporates upon contact with skin. The compositions preferably contain an acid neutralizing effective amount of ammonium hydroxide or DMAE.

Another embodiment of the present invention provides compositions which include:
(A) a retinoid and preferably retinol;
(B) a dermatologically active acid;
(C) a volatile base; and
(D) at least one second neutralizing agent.

According to yet another embodiment of the present invention, there are provided compositions which include:
(A) retinol; and
(B) a neutralized ammonium salt of a dermatologically active acid (e.g. the ammonium salt formed by a volatile compound comprising an amine such as ammonium hydroxide or a volatile alkanolamine such as DMEA). Examples of such salts include ammonium glycolate and $N_1N$-dimethylethanolammonium glycolate. Optionally, a second neutralized salt of a dermatologically active acid is included in the compositions.

Further provided are methods for reducing fine lines, wrinkles, skin roughness, and pore size and for increasing the clarity of a skin surface, cellular turnover, skin radiance and skin smoothness in an animal, for example, a mammal, such as a human, in need thereof. Compositions as described above are administered topically to the skin of the animal.

Methods for preparing the compositions above are also provided.

Other features and advantages of the invention will be apparent from the detailed description of the invention, the drawings, and the claims.

DETAILED DESCRIPTION OF THE INVENTION

In one embodiment, the present formulations provide compositions which have a storage pH of about 5 or higher. This provides storage stability for the retinoid compound (e.g. retinol). However, the pH of these compositions drops to below 5 when applied to the skin. This allows the hydroxy acid(s) and/or other skin beneficial acids(s) therein to become active upon application of the composition to the skin.

Retinoids suitable for use in the present invention preferably are unstable or pH sensitive in that they are chemically and physically unstable at relatively low pH such as, for example a pH below about 5, such as retinol and derivatives thereof. Suitable retinoids include, but are not limited to retinol and derivatives thereof, such as retinyl palmitate and retinyl acetate; retinaldehyde; and like compounds that bind to retinoid receptors.

Retinal is also known as vitamin A alcohol. Retinol is chemically and physically unstable at a pH below about 5. It is useful in reducing fine lines at wrinkles in skin. It is also useful in reducing mottled hyperpigmentation of skin. Other retinoids having pH dependent stability may also be used in combination with or in place of retinol in the present invention.

The dermatologically active acid may be a cosmetically active acid or a pharmaceutically active acid, such as, for example, a hydroxy acid, ascorbic acid or a derivative thereof, lipoic acid, dihydrolipoic acid, or a combination thereof.

Hydroxy acids useful in the present invention are either alpha- or beta-hydroxy acids, poly-hydroxy acids, or any combinations of any of the foregoing. Preferably, the hydroxy acid is an alpha-hydroxy acid. Examples of alpha hydroxy acids include, but are not limited to lactic acid, glycolic acid, malic acid, tartaric acid, pyuric acid, citric acid, or any combination of any of the foregoing. Special mention is made of glycolic acid.

Beta-hydroxy acids include, but are not limited to, salicylic acid.

Other suitable hydroxy acids are disclosed in U.S. Pat. No. 5,889,054, which is hereby incorporated by reference.

Other acids suitable for use in the present invention include, but are not limited to, ascorbic acid and derivatives thereof, lipoic acid, and dihydrolipoic acid. Suitable ascorbic acid derivatives include, but are not limited to, magnesium ascorbyl phosphate; sodium ascorbyl phosphate; sodium ascorbate; and ascorbyl glucosides.

Suitable second neutralizing agents which may be included in the composition include, but are not limited to, alkali hydroxides, such as sodium hydroxide and potassium hydroxide; and organic bases, such as alkanolamines, including, but not limited to, diethanolamine, triethanolamine, DMAE and aminobutanol; ammonium hydroxide, and amino acids, including, but not limited to, arginine and lysine; and any combination of any of the foregoing. A preferred second neutralizing agent is sodium hydroxide.

When utilized, ammonium hydroxide is typically added as a solution containing from about 27 to about 31 percent by weight of ammonium hydroxide based upon 100 percent by weight of total ammonium hydroxide solution.

The compositions of the present invention may also include other adjuvants, such as, for example, vehicles including, but not limited to, water or alcohol; humectants, including, but not limited to, glycerin; buffering agents including, but not limited to, citric acid and sodium citrate; viscosity adjusters, including, but not limited to, carbomer gelling agents, gum derivatives, and other viscosity controlling, decreasing, and increasing agents; preservatives including, but not limited to, parabens, such as methylparaben and propylparaben, and phenoxyethanol; emulsifiers including, but not limited to, polysorbate 80, glyceryl distearate, POE 10 stearyl ether, steareth 10, ceateareth 20 and stearyl alcohol, and ceteareth 20 and cetearyl alcohol; conditioning agents including, but not limited to, octyl hydroxystearate, stearyl alcohol, lactose, and dimethicone; emollients including, but not limited to, cholesterol NF, petrolatum, mineral oils and esters including, but not limited to, isopropyl myristate, isopropyl palmitate, 1-decene polymer (hydrogenated), and $C_{12}$-$C_{15}$ alcohol benzoates; thickeners, including, but not limited to, binders, polyacrylamide, $C_{13}$-$C_{14}$ isoparafin, and laureth-7; antioxidants, including, but not limited to ascorbic acid, butylated hydroxytoluene (BHT), tocopheryl acetate, and the like; UV stabilizers; UV radiation absorbers (sunscreen filters); fragrances; colorants; chelating agents, including, but not limited to, disodium ethylenediaminetetraacetate (EDTA); or any combinations of any of the foregoing. Examples of these adjuvants are disclosed in the International Cosmetic Ingredient Dictionary and Handbook, 7$^{th}$ Ed. (1997)

These compositions can be formulated as creams, gels, or liquids, and preferably are prepared as lotions. These compositions can be prepared as liposomes, including, but not limited to, unilamellar, multilamellar, or paucilamellar vesicles; nanospheres; microsponges; emulsions, such as a multiple emulsion and a cleansing emulsion; or any combination of any of the foregoing by methods known to those skilled in the art. In one embodiment, the composition is prepared as a paucilamellar vesicle (e.g. containing the retinoid and/or the dermatologically active acid or salt thereof) having, for example, between 2 and 10 lipid bilayers and a lipophilic core which may contain an apolar oil or wax.

The compositions are typically neutralized to a pH above about 4.5, preferably ranging from about 4.5 to about 8 and most preferably from about 5 to about 6. The amount of the volatile base (e.g. ammonium hydroxide or DMAE) and optionally second neutralizing agent useful herein is that amount sufficient to adjust the pH of the compositions to the above pH ranges. The amount of volatile base in the compositions of the present invention is preferably that amount sufficient to adjust the pH of the acid from about 4.0 or less to at least about 5.

A preferred method of preparation includes neutralizing the composition to a pH of about 4.0 or less with the aforementioned second neutralizing agent and then further neutralizing the composition to a pH of at least about 5 with the volatile base.

The amount of retinoid in these compositions is typically a fine line-, wrinkle-, or mottled pigmentation-reducing effective amount. The amount of retinoid (e.g., retinol) is at least about 0.001 percent by weight, (e.g., about 0.01 to about 10 percent, such as about 0.01 to about 1 percent), based upon 100 percent by weight of total composition.

The amount of acid, ammonium salt of acid, or other salt of the acid is typically a skin surface clarity, cellular turnover-, skin radiance-, skin smoothness-, skin permeation-, or collagen synthesis-increasing effective amount. Preferably, this amount ranges from about 0.1 to about 20 percent by weight based upon 100 percent by weight of total composition. More preferably this amount ranges from about 1 to about 12 percent by weight, and most preferably, this amount is from about 4 to about 8 percent by weight, based upon 100 percent by weight of total composition.

The composition preferably contains from about 1 to about 99 percent, and more preferably from about 60 to about 95 percent by weight of water, based upon 100 percent by weight of total composition.

Generally, the composition contains sufficient thickener to impart body to the composition without causing it to become so viscous as to hinder spreadability of the composition. The composition also preferably contains up to about 5 percent by weight of a viscosity adjuster, up to about 20 percent by weight of an emollient, from about 0.1 to about 10 percent by weight of an emulsifier, up to about 5 percent by weight of a spreading agent, up to about 10 percent by weight of a thickener, a preservative, a chelating agent, and a humectant, based upon 100 percent weight of total composition. More preferably, the composition contains from about 0.1 to about 2 percent by weight of a viscosity adjuster, from about 3 to about 5 percent by weight of an emulsifier, from about 1 to about 2 percent by weight of a spreading agent, an antimicrobially effective amount of a preservative, and from about 3 to about 5 percent by weight of a thickener, based upon 100 percent weight of total composition.

Without being bound by any theory, applicants believe that by using a salt of the acid and a volatile base, the storage pH of the present composition can remain above 5, thereby providing a stable atmosphere for the retinol or any other pH sensitive ingredient. However, when applied to the skin, the pH of the salt of the acid changes by volatilization of the volatile base (e.g., the ammonium). The pH then drops to a range in which the acid can cause beneficial changes.

The compositions can be applied topically to a mammal, and preferably a human, in need of a retinoid, acids, or a combination thereof. Typically, the amount applied will be that amount effective to accomplish the purpose of application.

The following examples illustrate the invention without limitation. All amounts are given as weight percentages based upon 100 percent by weight of total composition unless noted otherwise.

EXAMPLE 1

A retinol/alpha-hydroxy acid composition having the formulation of Table 1 and a pH of about 6 and containing paucilamellar vesicles was prepared by a shear mixing method. The apparatus used to prepare the liposomes by the shear mixing method is described in U.S. Pat. No. 4,895,452, which is hereby incorporated by reference. A mixture containing the appropriate amounts of the ingredients for the lipid phase was heated in a container at about 75° C. until all of the lipids melted. The lipid melt was then cooled to about 65° C. The ingredients for the aqueous phase were mixed together, heated to about 75° C. to dissolve them, and then cooled to about 60° C. The lipid melt and aqueous phase mixture were then poured into separate holding reservoirs of the shear mixing apparatus.

The positive displacement pump for the lipid melt and aqueous phase mixture feed lines were turned on. The feed rate was adjusted to 1 part lipid to 4 parts aqueous phase.

The aqueous phase mixture and lipid melt were fed through injection jets into a cylindrical mixing chamber tangentially with respect to the cylinder wall. In the mixing chamber, the two streams of flowing liquid intersect in such a manner as to cause shear mixing that leads to the formation of liposomes. The liposomes formed were then withdrawn through an exit tube and transferred to a Cafero mixing vesicle. The liposomes were cooled to 40° C., under mixing at 200 rpm. After cooling, the single addition components listed in Table 1, were added sequentially. The resultant mixture was then mixed at 200 rpm for about 30 minutes. The formulation was allowed to cool to room temperature under ambient conditions.

TABLE 1

Retinol/Alpha-Hydroxy Acid Liposome Formulation-pH6

| TRADE NAME | CHEMICAL NAME | FUNCTION | % WT/WT |
|---|---|---|---|
| AQUEOUS PHASE | | | |
| Deionized Water | D. I. Water | Vehicle | 60.93 |
| Glycerin 916 | Glycerin | Humectant | 4 |
| Citric Acid | Citric Acid | Buffering Agent | 0.13 |
| Sodium Citrate | Sodium Citrate | Buffering Agent | 0.5 |
| Sodium Chloride | Sodium Chloride | Viscosity Adjuster | 0.1 |
| Methyl Parasept | Methylparaben | Preservative | 0.25 |
| Propyl Parasept | Propylparaben | Preservative | 0.15 |
| Tween 80 | Polysorbate 80 | Emulsifier | 0.7 |
| Glypure (70%) | Glycolic Acid | Skin Conditioner | 5.71 |
| NH4OH^ | Ammonium Hydroxide (27 to 31% Solution) | pH Adjuster (pH = 6) | 3.2 |
| LIPID PHASE | | | |
| Wickenol 171 | Octyl Hydroxystearate | Conditioning Agent | 5.8 |
| Kessco GDS | Glyceryl Distearate | Emulsifier | 2.8 |
| Cholesterol, NH | Cholesterol NF | Emulsifer | 1 |
| BRIJ 76 | POE 10 Stearyl Ether | Emulsifer | 1.4 |
| Protocol ST 20G | Ceteareth 20 and Stearyl Alcohol | Emulsifier | 3 |
| Protocol CS 20D | Ceteareth 20 and Stearyl Alcohol | Emulsifier | 3 |
| Stearyl Alcohol | Stearyl Alcohol | Skin Conditioner | 0.5 |
| Retinol 50CJ** | V Retinol in Polysorbate-20 | Skin Conditioner | 0.4 |
| BHT | BHT | Antioxidant | 0.1 |
| Vitamin E Acetate | Tocopheryl Acetate | Antioxidant | 0.1 |

TABLE 1-continued

Retinol/Alpha-Hydroxy Acid Liposome Formulation-pH6

| TRADE NAME | CHEMICAL NAME | FUNCTION | % WT/WT |
|---|---|---|---|
| SINGLE ADDITION COMPONENTS | | | |
| Emeressence 1160 | Phenoxyethanol | Preservative | 0.73 |
| Dimethicone 47V | 100 Centistoke Dimethicone | Skin Conditioner | 2.5 |
| Sepigel 305 | Polyacrylamide, C13-24 Isoparrifin and Laureth-7 | Thickener | 3 |

**Retinol 50CJ is available from BASF of Mount Olive, NJ, and contains 50% by weight of retinol.
^Amount of NH₄OH required to reach pH of 6 is estimated; each batch will be titrated to pH = 6.

The formulation was applied to the skin, and the pH of the skin was measured over time. Results are illustrated in FIG. 1. The pH of the preparation dropped to about 4.1 within 15 minutes of application. This reduced the skin pH to about 4.

COMPARATIVE EXAMPLE 1A

A retinol/alpha-hydroxy acid containing composition having the formulation of Table 2 and a pH of about 4 was prepared as described in Example 1. The amount of ammonium hydroxide in this composition was approximately half the amount incorporated in the composition of Example 1.

TABLE 2

Retinol/Alpha-Hydroxy Acid Liposome Formulation - pH 4

| TRADE NAME | CHEMICAL NAME | FUNCTION | % WT/WT |
|---|---|---|---|
| AQUEOUS PHASE (qs with DI water) | | | |
| Deionized Water | D. I. Water | Vehicle | 62.43 |
| Glycerin 916 | Glycerin | Humectant | 4 |
| Citric Acid | Citric Acid | Buffering Agent | 0.13 |
| Sodium Citrate | Sodium Citrate | Buffering Agent | 0.5 |
| Sodium Chloride | Sodium Chloride | Viscosity Adjuster | 0.1 |
| Methyl Parasept | Methylparaben | Preservative | 0.25 |
| Propyl Parasept | Propylparaben | Preservative | 0.15 |
| Tween 80 | Polysorbate 80 | Emulsifier | 0.7 |
| Glypure (70%) | Glycolic Acid | Skin Conditioner | 5.71 |
| NH₄OH^ | Ammonium Hydroxide 27 to 31% Solution | pH Adjuster (pH = 4) | 1.7 |
| LIPID PHASE | | | |
| Wickenol 171 | Octyl Hydroxystearate | Conditioning Agent | 5.8 |
| Kessco GDS | Glyceryl Distearate | Emulsifier | 2.8 |
| Cholesterol, NH | Cholesterol NF | Emollient | 1 |
| BRIJ 76 | POE 10 Stearyl Ether | Emulsifer | 1.4 |
| Protocol ST 20G | Ceteareth 20 and Stearyl Alcohol | Emulsifier | 3 |
| Protocol CS 20D | Ceteareth 20 and Stearyl Alcohol | Emulsifier | 3 |
| Stearyl Alcohol | Stearyl Alcohol | Skin Conditioner | 0.5 |
| Retinol 50CJ** | Retinol in Polysorbate-20 | Skin Conditioner | 0.4 |
| BHT | BHT | Antioxidant | 0.1 |
| Vitamin E Acetate | Tocopheryl Acetate | Antioxidant | 0.1 |

TABLE 2-continued

Retinol/Alpha-Hydroxy Acid Liposome Formulation - pH 4

| TRADE NAME | CHEMICAL NAME | FUNCTION | % WT/WT |
|---|---|---|---|
| SINGLE ADDITION COMPONENTS | | | |
| Emeressence 1160 | Phenoxyethanol | Preservative | 0.73 |
| Dimethicone 47V | 100 Centistoke Dimethicone | Skin Conditioner | 2.5 |
| Sepigel 305 | Polyacrylamide, $C_{13-24}$ Isoparrifin and Laureth-7 | Thickener | 3 |

**Retinol 50CJ is available from BASF of Mount Olive, NJ, and contains 50% by weight of retinol.
Amount of $NH_4OH$ required to reach pH of 4 is estimated.

The formulation was applied to skin, and the pH of the skin was measured over time. Results are illustrated in FIG. 1.

COMPARATIVE EXAMPLE 1B

A retinol/alpha-hydroxy acid containing composition was prepared as described in Example 1 above, except sodium hydroxide was substituted for the ammonium hydroxide.

The formulation was applied to skin, and the pH of the skin was measured over time. Results are illustrated in FIG. 1.

COMPARATIVE EXAMPLE 1C

An alpha-hydroxy acid containing composition having 8 percent by weight sodium glycolate at a pH of about 3.5 and no retinol was prepared as described in Example 1 above.

The formulation was applied to skin, and the pH of the skin was measured over time. Results are illustrated in FIG. 1.

EXAMPLE 2

A composition containing 0.15 percent by weight of retinol and 4 percent by weight of glycolic acid, neutralized with ammonium hydroxide to a pH of about 6, was prepared as described in Example 1 above.

An in vivo study of proliferative activity on skin was conducted. The marker of proliferative activity is an increase in fluorescent signal in the ultraviolet portion of the light spectrum. Over the course of 11 days of application, the fluorescence of the epidermis (exciting with 296 nm radiation, monitoring fluorescence at 340 nm) increases with increased proliferation activity. This fluorescence marker also increases after another proliferation inducing treatment such as tape-stripping, and has been shown to correlate with increased cell turnover-rate as measured by increased loss of epidermal stain, dansyl chloride.

Figure 2:
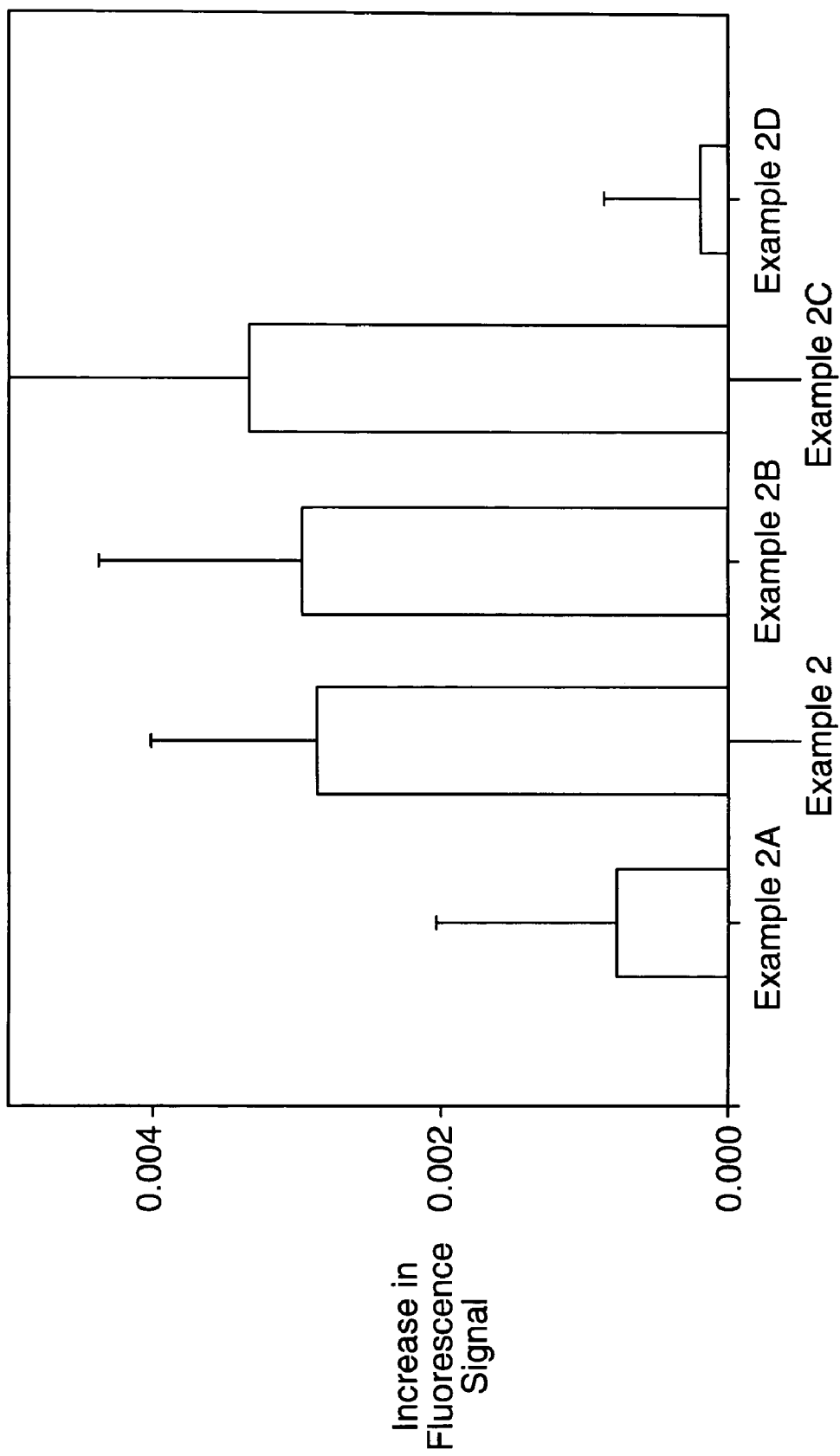
FIG. 2 is a graphic illustration of cell proliferation measured as slope of fluorescence after treatment.

The slope of the increased fluorescence is illustrated in FIG. 2.

COMPARATIVE EXAMPLE 2A

An in vivo study as described in Example 2 was conducted using a preparation containing no glycolic acid or retinol at pH 6 (placebo).

The slope of the increased fluorescence is illustrated in FIG. 2.

COMPARATIVE EXAMPLE 2B

An in vivo study as described in Example 2 was conducted using a preparation containing 4 percent by weight of partially neutralized glycolic acid at pH 4 without retinol (Avon ANEW®).

The slope of the increased fluorescence is illustrated in FIG. 2.

COMPARATIVE EXAMPLE 2C

An in vivo study as described in Example 2 was conducted using a preparation containing 8 percent by weight of glycolic acid partially neutralized at pH 3.8 without retinol (Neutrogena HEALTHY SKIN®).

The slope of the increased fluorescence is illustrated in FIG. 2.

COMPARATIVE EXAMPLE 2D

An in vivo study as described in Example 2 was conducted on untreated skin.

The slope of the increased fluorescence is illustrated in FIG. 2.

FIG. 2 illustrates a significant increase in fluorescence activity and, therefore, cell proliferation in the retinol/glycolic acid preparation of Example 2 in comparison with both a placebo (Example 2A) and untreated skin (Example 2D).

FIG. 2 also illustrates a significant increase in fluorescence activity and, therefore, cell proliferation in the retinol/glycolic acid preparation of Example 2 which is similar to that of glycolic acid containing products having pH=s of about 4 (Comparative Examples 2B-D).

EXAMPLE 3

A composition containing 0.15 percent by weight of retinal and 4 percent by weight of glycolic acid neutralized to pH 5.5 with ammonium hydroxide as in Example 1 was prepared.

Figure 3:
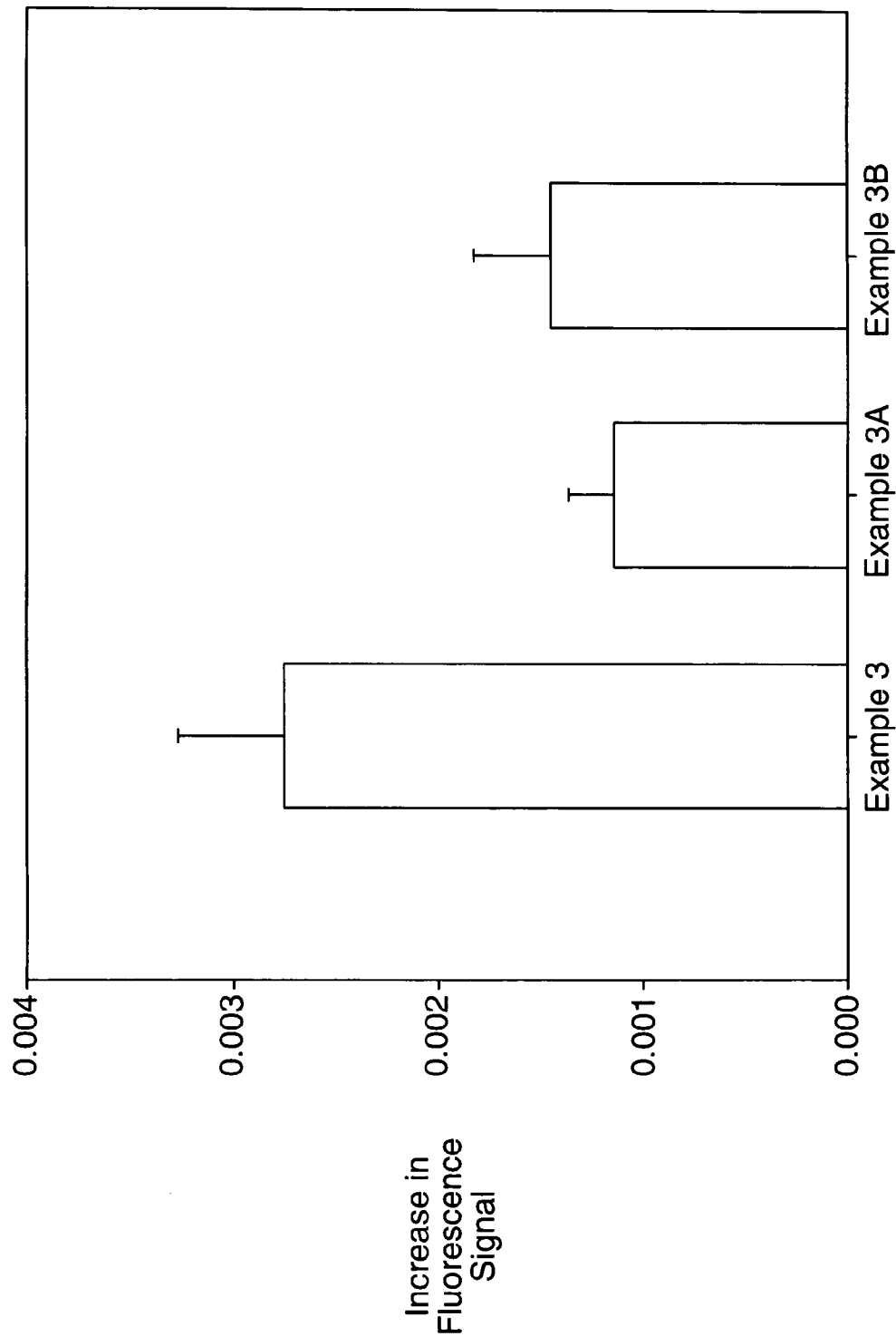
FIG. 3 is a graphic illustration comparing the activity of ammonium hydroxide and sodium hydroxide neutralized alpha-hydroxy acids in combination with retinol.

Fluorescence was measured as in Example 2. Results are illustrated in FIG. 3.

COMPARATIVE EXAMPLE 3A

A composition containing 0.15 percent by weight of retinol and 4 percent by weight of glycolic acid neutralized to pH 5.5 with sodium hydroxide as in Example 1 was prepared.

Fluorescence was measured as in Example 2. Results are illustrated in FIG. 3.

COMPARATIVE EXAMPLE 3B

The fluorescence of untreated skin was measured as in Example 2. Results are illustrated in FIG. 3.

FIG. 3 illustrates that while ammonium glycolate (Example 3) dissociates when applied to the skin, sodium glycolate apparently does not (Comparative Example 3A). The latter results in little change in proliferative activity of the skin, and thus no apparent skin benefit.

EXAMPLE 4

A composition prepared as in Example 1 was stored for 13 weeks at 40° C. (simulating 2 years of ambient aging). This preparation retained 87% of the original retinol content after storage.

COMPARATIVE EXAMPLE 4A

A composition prepared in Comparative Example 1A was stored for 13 weeks at 40° C. (simulating 2 years of ambient aging). This preparation retained only 52% of the original retinol content after storage.

EXAMPLE 5

A retinol/alpha-hydroxy acid containing composition having the formulation of Table 3 and containing paucilamellar vesicles was prepared as in Example 1 above. After the single addition components were added, a slurry of water and Cabopol ETD 2020 was added to the composition. Mirasil DM 100 and Phenoxetol were added thereto sequentially under mixing at 200 rpm for about 30 minutes. The formulation was allowed to cool to about 25 E C under ambient conditions. The composition did not contain ammonium hydroxide.

TABLE 3

| TRADE NAME | CHEMICAL NAME | FUNCTION | % WT/WT |
|---|---|---|---|
| LIPID PHASE | | | |
| Brij 76 | Steareth-10 | Emulsifier | 1.4 |
| Kessco GDS | Glyceryl Distearate | Emulsifier | 2.8 |
| Cholesterol NF | Cholesterol | Emulsifier | 1 |
| Procol ST 20G | Ceteareth-20 & Stearyl Alcohol | Emulsifier | 3 |
| Procol CS 20D | Cereareth-20 & Cetearyl Alcohol | Emulsifier | 3 |
| Lanol S | Stearyl Alcohol | Skin Conditioner | 0.5 |
| Wickenol 171 | Octyl Hydroxystearate | Conditioning Agent | 5.8014 |
| BHT | BHT | Antioxidant | 0.1 |
| Tween 80 | Polysorbate 80 | Emulsifier | 0.7 |
| Retinol 50CJ** | Retinol in Polysorbate-20 | Skin Conditioner | 0.25 |
| AQUEOUS PHASE | | | |
| Eau purifiee | Aqua | Vehicle | 41.0843 |
| Pricerin 9099 | Glycerin | Humectant | 4 |
| Methylparaben | Methylparaben | Preservative | 0.25 |
| Propylparaben | Propylparaben | Preservative | 0.15 |
| Disodium EDTA | Disodium EDTA | Chelator | 0.1 |
| Lactose Rectapur | Lactose | Humectant | 5 |
| Glypure 70% | Glycolic acid (70%) | Skin Conditioner | 5.7143 |
| Sodium Hydroxide | Sodium Hydroxide | pH Adjuster | 1.32 |
| Eau purifiee | Aqua | Vehicle | 20 |
| Carbopol ETD 2020 | Acrylates/C10-30 Alkyl Acrylate crosspolymer | Thickener | 0.6 |
| SINGLE ADDITION COMPONENTS | | | |
| Mirasil DM 100 | Dimethicone | Skin Conditioner | 2.5 |
| Phenoxetol | Phenoxyethanol | Preservative | 0.73 |

**Retinol 50CJ is available from BASF of Mount Olive, NJ, and contains 50% by weight of retinol.

Figure 4:
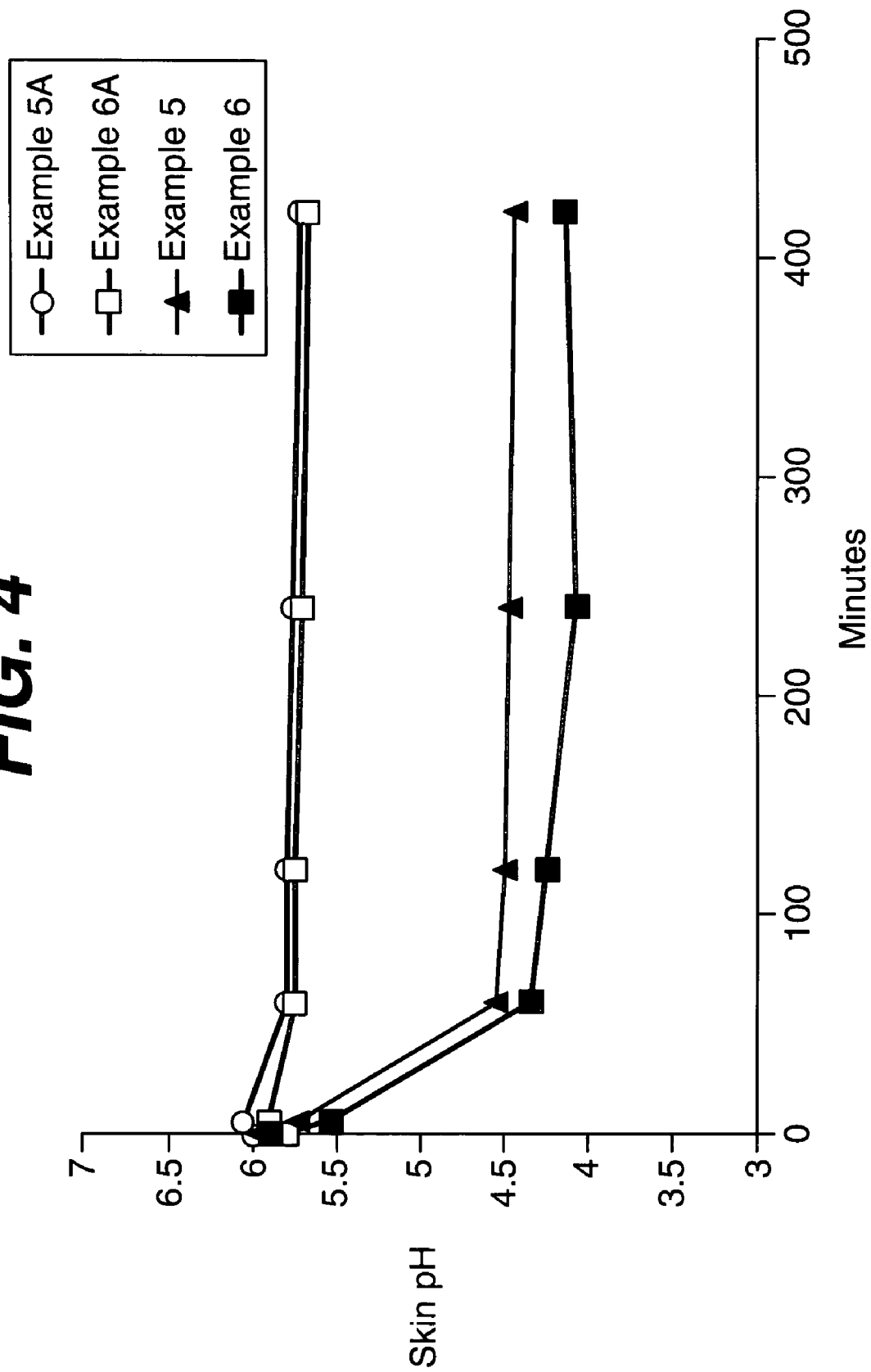
FIG. 4 is a graphic illustration of skin pH over time before and after treatment.

A control having the formulation of Table 3 was prepared excluding ammonium hydroxide and sodium hydroxide (Example 5A). The composition and control were applied to skin, and the pH of the skin was measured over time. Results are illustrated in FIG. 4.

EXAMPLE 6

A retinol/alpha-hydroxy acid containing composition having the formulation of Table 4 and a pH of about 5.8 was prepared as described in Example 5, except 3% by weight of ammonium hydroxide was substituted for the sodium hydroxide in Example 5.

TABLE 4

| TRADE NAME | CHEMICAL NAME | FUNCTION | % WT/WT |
|---|---|---|---|
| Brij 76 | Steareth-10 | Emulsifier | 1.4 |
| LIPID PHASE | | | |
| Kessco GDS | Glyceryl Distearate | Emulsifier | 2.8 |
| Cholesterol NF | Cholesterol | Emulsifier | 1 |
| Procol ST 20G | Ceteareth-20 & Stearyl Alcohol | Emulsifier | 3 |
| Procol CS 20D | Cereareth-20 & Cetearyl Alcohol | Emulsifier | 3 |
| Lanol S | Stearyl Alcohol | Emulsifier | 0.5 |
| Wickenol 171 | Octyl Hydroxystearate | Emulsifier | 5.8014 |
| BHT | BHT | Antioxidant | 0.1 |
| Tween 80 | Polysorbate 80 | Emulsifier | 0.7 |
| Retinol 50CJ** | Retinol in Polysorbate-20 | Skin Conditioner | 0.25 |
| Eau purifiee | Aqua | Vehicle | 39.4043 |
| AQUEOUS PHASE | | | |
| Pricerin 9099 | Glycerin | Humectant | 4 |
| Methylparaben | Methylparaben | Preservative | 0.25 |
| Propylparaben | Propylparaben | Preservative | 0.15 |
| Disodium EDTA | Disodium EDTA | Chelator | 0.1 |
| Lactose Rectapur | Lactose | Humectant | 5 |
| Glypure 70% | Glycolic acid (70%) | Skin Conditioner | 5.7143 |
| Ammonium Hydroxide | Ammonium Hydroxide (30%) | pH Adjuster | 3 |
| Eau purifiee | Aqua | Vehicle | 20 |
| Carbopol ETD 2020 | Acrylates/C10-30 Alkyl Acrylate crosspolymer | Thickener | 0.6 |
| SINGLE ADDITION COMPONENTS | | | |
| Mirasil DM 100 | Dimethicone | Skin Conditioner | 2.5 |
| Phenoxetol | Phenoxyethanol | Preservative | 0.73 |

**Retinol 50CJ is available from BASF of Mount Olive, NJ, and contains 50% by weight of retinol.

A control having the formulation of Table 4 was prepared excluding ammonium hydroxide (Example 6A). The composition and control were applied to skin, and the pH of the skin was measured over time. Results are illustrated in FIG. 4.

EXAMPLES 7 AND 8

Two retinol/alpha-hydroxy acid containing liposomal compositions having the formulations of Table 5 below are prepared as follows.

TABLE 5

| TRADE NAME | CHEMICAL NAME | Function | Example 7 (% W/W) | Example 8 (% W/W) | Ranges |
|---|---|---|---|---|---|
| LIPID PHASE | | | | | |
| Glyceryl Dilaurate | Glyceryl Dilaurate | Nonionic Surfactant | 2.8 | 2.8 | 1.4-8.4 |

TABLE 5-continued

| TRADE NAME | CHEMICAL NAME | Function | Example 7 (% W/W) | Example 8 (% W/W) | Ranges |
|---|---|---|---|---|---|
| Cholesterol | Cholesterol | Nonionic Surfactant | 0.9 | 0.9 | 0.45-2.7 |
| POE 10 Stearyl Alcohol | POE 10 Stearyl Alcohol | Nonionic Surfactant | 2.5 | 2.5 | 1.25-7.5 |
| Laureth-9 | Laureth-9 | Nonionic Surfactant | 1.24 | 1.24 | 0.62-3.72 |
| Butylated Hydroxytoluene (BHT) | BHT | Anti-oxidant | 0.05 | 0.05 | 0-3 |
| Retinol 50C ™ | Retinol in Polysorbate-20 | Skin Conditioner | 0.2 | 0.4 | 0.01-2 |
| AQUEOUS PHASE | | | | | |
| Citric Acid | Citric Acid | Anti-oxidant | 0.4 | 0.4 | 0.1-0.8 |
| Trisodium Citrate dihydrate | Trisodium Citrate dihydrate | Buffer | 0.6 | 0.6 | 0.1-0.8 |
| Ascorbic Acid | Ascorbic Acid | Anti-oxidant | 0.01 | 0.01 | 0.01-0.1 |
| Glycerin | Glycerin | Humectant | 0 | 4.0 | 0-20 |
| Disodium EDTA | Disodium EDTA | Chelating Agent Preservative | 0.2 | 0.2 | 0.01-0.2 |
| Phenoxyethanol | Phenoxyethanol | Preservative | 0.5 | 0.5 | 0.01-0.5 |
| Methylparaben | Methylparaben | Preservative | 0.25 | 0.25 | 0.01-0.2 |
| Propylparaben | Propylparaben | Preservative | 0.15 | 0.15 | 0.01-0.2 |
| Glypure (70%) | | Skin Conditioner | 5.71 | 5.71 | 0.01-15 |
| Ammonium Hydroxide (27 to 31%) | Ammonium Hydroxide (27 to 31%) | pH adjuster (pH = 6) | 3.2 | 3.2 | 0.01-10 |
| Water | Water | Carrier | 81.29 | 77.06 | 40-90 |

These compositions may be prepared by the following two methods.

1. Shear Mixing Method: Appropriate amounts of the lipid phase ingredients are mixed in a container heated to about 75° C. until all the lipids have melted. The lipid melt is then cooled to about 65° C. The aqueous phase ingredients are mixed and heated to about 75° C. to dissolve them and then cooled to about 60° C. The lipid melt and aqueous phase mixture are poured into separate holding reservoirs of a shear mixing apparatus for preparing liposomes as described in U.S. Pat. No. 4,895,452. The positive displacement pump for the lipid and aqueous feed lines is turned on. The feed rate will depend on the desired viscosity of the composition. For a thinner consistency, a feed rate of 1 part lipid to 9 parts aqueous phase may be utilized. For thicker consistencies, a feed rate of 1 part lipid phase to 4 parts aqueous phase may be utilized. After the feed rate is adjusted, valves to the feed lines are opened and the aqueous phase mixture and lipid melt are fed through injection jets into a cylindrical mixing chamber tangentially with respect to the cylinder wall. In the mixing chamber, the two streams of liquid intersect in such a manner as to cause shear mixing that causes the formation of liposomes. The liposomes are then withdrawn through an exit tube.

2. Syringe Method: Appropriate amounts of the lipid phase ingredients are mixed in a beaker at 75° C. until the lipids melt. The lipid melt is drawn into a syringe, which was preheated in a water bath to about 75° C. A second syringe containing appropriate amounts of the aqueous phase ingredients is preheated in a water bath to about 70° C. The two syringes were then connected via a 3-way metal stopcock. The ratio of aqueous phase mixture to lipid phase mixture was about 4:1 or 4 ml of aqueous phase mixture to 1 ml of lipid phase mixture. The ratio of aqueous phase mixture to lipid phase mixture can be adjusted to obtain the desired viscosity. After injecting the aqueous phase mixture into the lipid phase mixture, the resulting mixture is rapidly mixed back and forth between the two syringes several times until the contents cool to about 25-30° C.

EXAMPLES 9 AND 10

Two oil-in-water emulsions of the present invention are shown in Table 6.

TABLE 6

| TRADE NAME | CHEMICAL NAME | Function | Example 9 (% W/W) | Example 10 (% W/W) | Ranges |
|---|---|---|---|---|---|
| OIL PHASE | | | | | |
| Cetearyl Glucoside | Cetearyl Glucoside | Surfactant | 1.4 | 1.4 | 0.1-2.8 |

TABLE 6-continued

| TRADE NAME | CHEMICAL NAME | Function | Example 9 (% W/W) | Example 10 (% W/W) | Ranges |
|---|---|---|---|---|---|
| C12-15 Alkyl Benzoate | C12-15 Alkyl Benzoate | Surfactant | 4.0 | 4.0 | 1-6 |
| Octyl Hydroxystearate | Octyl Hydroxystearate | Emollient | 1.0 | 1.0 | 0-5 |
| Dimethicone | Dimethicone | Spreading Agent | 1.0 | 1.0 | 0-5 |
| Cyclomethicone | Cyclomethicone | Spreading Agent | 1.0 | 1.0 | 0-5 |
| Cetyl Alcohol | Cetyl Alcohol | Emollient | 2.5 | 2.5 | 0-4 |
| Butylated Hydroxytoluene | BHT | Anti-oxidant | 0.05 | 0.05 | 0-3 |
| Octyl Methoxycinnamate | Octyl Methoxycinnamate | Sunscreen | 6.0 | 6.0 | 0-10 |
| Propylparaben | Propylparaben | Preservative | 0.5 | 0.1 | 0-0.5 |
| Vitamin E acetate | Vitamin E acetate | Anti-oxidant | 0.5 | 0.5 | 0-0.5 |
| Retinol | Retinol | Anti-Wrinkle | 0.25 | 0.4 | 0.01-5 |
| Tocopherol Acetate | Tocopherol Acetate | Anti-oxidant | 0.5 | 0.5 | 0-0.5 |
| AQUEOUS PHASE | | | | | |
| Glycerin | Glycerin | Humectant | 3.0 | 3.0 | 0-20 |
| D-Pathenol | D-Pathenol | Pro-Vitamin | 0.5 | 0.5 | 0-5 |
| Disodium EDTA | Disodium EDTA | Chelator, whitening agent | 0.1 | 0.1 | 0.01-1 |
| Methyl Paraben | Methyl Paraben | Preservative | 0.2 | 0.2 | 0-0.3 |
| Carbomer | | Thickener | 0.35 | 0.35 | 0-3 |
| Glycolic acid (70%) | Glycolic acid (70%) | Skin Conditioner | 5.71 | 5.71 | 0-15 |
| Ammonium Hydroxide | Ammonium Hydroxide | pH adjuster | 3.2 | 3.2 | 0-1 |
| Deionized Water | Deionized Water | Carrier | 68.19 | 68.04 | 50-80 |

Each emulsion is prepared by mixing the oil phase ingredients and heating the mixture to about 85° C. The oil phase mixture is then cooled to about 60° C.

In a separate vessel, the carbomer is slowly added to the water. After mixing for about 10 minutes the remaining aqueous phase ingredients are added and the mix is heated to about 60° C.

The two phases are then combined, mixed for about 10 minutes, and cooled to room temperature. One or more depigmentation agents may be added to the formulations in these examples.

EXAMPLES 11 AND 12

Two water-in-oil emulsions of the present invention are shown in Table 7.

TABLE 7

| TRADE NAME | CHEMICAL NAME | Function | Example 11 (% W/W) | Example 12 (% W/W) | Preferred Ranges |
|---|---|---|---|---|---|
| OIL PHASE | | | | | |
| Mineral Oil | Mineral Oil | Emollient | 25.0 | 25.0 | 40-80 |
| Sorbitan Monooleate | Sorbitan Monooleate | Surfactant | 5.0 | 5.0 | 1-6 |
| Stearyl Alcohol | Stearyl Alcohol | Emollient | 25.0 | 25.0 | 20-60 |
| Dimethicone | Dimethicone | Spreading Agent | 1.0 | 1.0 | 1-5 |
| Cetyl Alcohol | Cetyl Alcohol | Emollient | 2.0 | 2.0 | 0.1-10 |
| Hydrogenated Lecithin | Hydrogenated Lecithin | Anti-oxidant | 3.0 | 3.0 | 0-10 |
| Parsol MCX | | Sunscreen | 3.0 | 3.0 | 0-10 |
| Butylated Hydroxytoluene | BHT | Anti-oxidant | 0.05 | 0.05 | 0-3 |
| Retinol | Retinol | Anti-Wrinkle | 0.25 | 0.4 | 0.01-5 |
| Propylparaben | Propylparaben | Preservative | 0.5 | 0.5 | 0.01-0.5 |
| Vitamin E acetate | Vitamin E acetate | Anti-oxidant | 0.5 | 0.5 | 0.01-0.5 |

TABLE 7-continued

| TRADE NAME | CHEMICAL NAME | Function | Example 11 (% W/W) | Example 12 (% W/W) | Preferred Ranges |
|---|---|---|---|---|---|
| AQUEOUS PHASE | | | | | |
| Glycerin | Glycerin | Humectant | 3.0 | 3.0 | 0-20 |
| Methyl Paraben | Methyl Paraben | Preservative | 0.2 | 0.2 | 0.01-0.3 |
| Water | Water | Carrier | 22.59 | 22.44 | 20-45 |
| Glycolic acid (70%) | Glycolic acid (70%) | Skin Conditioner | 5.71 | 5.71 | 0-15 |
| Ammonium Hydroxide | Ammonium Hydroxide | pH adjuster | 3.2 | 3.2 | 0-1 |

Each emulsion is prepared by melting stearyl alcohol and mineral oil at about 70° C. The other oil phase ingredients are added and the mixture is heated to about 75° C. The aqueous phase ingredients are dissolved in water and warmed to about 70° C. The aqueous phase mixture is added to the oil phase mixture. The resulting mixture is stirred until it congeals.

EXAMPLE 13

An oil-in-water emulsion of the present invention is shown in Table 8.

The emulsion is prepared by mixing the oil phase ingredients and heating the mixture to about 85° C. The oil phase mixture is then cooled to about 60° C. In a separate vessel, the water phase ingredients are added, mixed and heated to about 60° C.

The two phases are then combined, mixed for about 10 minutes, and cooled to about 35° C., at which time the post additions are added and mixed, followed by the addition and mixing of the glycolic acid/malic acid/deionized water buffer pre-mix. The retinol 50C is then added and mixed last.

TABLE 8

| CTFA Name | Trade Name | FUNCTION | Wt. % |
|---|---|---|---|
| OIL PHASE | | | |
| C12-15 Alkyl Benzoate | Finsolv TN | Solubilizing Agent | 4.00 |
| Octyl Hydroxystearate | Wickenol 171 | emolient | 1.00 |
| Dimethicone, 100 centistoke | Dimethicone 47V-100 | emolient | 1.00 |
| Steareth 2 | Brij 72 | emulsifier | 0.60 |
| Cetyl Alcohol | Cetal | emolient, emulsifier | 2.50 |
| Steareth 20 | Brij 721 | emulsifier | 0.90 |
| BHT | BHT | antioxidant for cosmetics | 0.10 |
| Pemulen TR1 | Acrylates/C10-30 Alkyl Acrylate Crosspolymer | thickener/ emulsifier | 0.50 |
| WATER PHASE | | | |
| Deionized Water | Water | Solvent | 62.59 |
| Disodium EDTA | EDTA | Chelating Agent | 0.10 |
| Glycerin | Glycerin 916 99.7% USP | humectant, emollient | 3.00 |
| Panthenol | D-Panthenol U.S.P. FCC | moisturizing agent | 0.50 |
| Phenoxyethanol | Emeressence 1160 | perservative | 0.73 |
| Methylparaben | Methylparaben | preservative | 0.35 |
| Propylparaben | Propylparaben | preservative | 0.17 |

TABLE 8-continued

| CTFA Name | Trade Name | FUNCTION | Wt. % |
|---|---|---|---|
| POST ADDITIONS | | | |
| DMAE/Tyrosine Pre-mix L-Tyrosine | L-Tyrosine | active | 0.50 |
| Deionized Water | Deionized Water | solvent | 15.00 |
| DMAE | 2-(dimethylamino)-ethanol | active | 3.00 |
| BUFFER PRE-MIX | | | |
| Glycolic Acid | Glypure 70 | buffer | 1.20 |
| Malic Acid | Malic Acid | buffer | 0.84 |
| Deionized Water | Deionized Water | Solvent | 1.32 |
| Retinol 50C | Vitamin A alcohol in Polysorbate 80 | vitamin A | 0.10 |

All patents, publications, applications, and test methods mentioned herein are hereby incorporated by reference.

Many variations of the present invention will suggest themselves to those skilled in the art in light of the above, detailed description. All such obvious variations are within the full intended scope of the appended claims.

The invention claimed is:

1. A composition comprising:
   (A) retinol;
   (B) a dermatologically active acid selected from the group consisting of lactic acid, glycolic acid, malic acid, tartaric acid, pyruvic acid, citric acid, salicylic acid, and ascorbic acid; and
   (C) 2-dimethylaminoethanol; wherein said composition has a pH of from about 5 to about 6 and wherein said retinol and said acid are stable and active upon application to the skin.

2. A composition as defined in claim 1, wherein said dermatologically active acid is ascorbic acid.

3. A composition as defined in claim 1, wherein said dermatologically active acid is glycolic acid.

4. A composition as defined in claim 1, wherein said dermatologically active acid is salicylic acid.

5. A composition as defined in claim 1, wherein said retinol comprises from about 0.01 to about 10 percent by weight, based upon 100 percent by weight of total composition.

6. A composition as defined in claim 5, wherein the amount of said dermatologically active acid ranges from about 0.1 to about 20 percent by weight, based upon 100 percent by weight of total composition.

7. A composition as defined in claim 3, said composition comprises from about 0.01 to about 10 percent by weight of retinol and from about 0.1 to about 20 percent by weight of said glycolic acid, based upon 100 percent of total composition.

8. A composition as defined in claim 4, said composition comprises from about 0.01 to about 10 percent by weight of retinol and from about 0.1 to about 20 percent by weight of said salicylic acid, based upon 100 percent of total composition.

9. A composition as defined in claim 1, further comprising a second neutralizing agent.

10. A composition as defined in claim 9, wherein said second neutralizing agent comprises an alkali hydroxide, alkanolamine, amino acid, or any combination of any of the foregoing.

11. A composition as defined in claim 10, wherein said second neutralizing agent comprises sodium hydroxide, potassium hydroxide, diethanolamine, triethanolamine, aminobutanol, arginine, lysine, or any combination of any of the foregoing.

12. A composition comprising:
(A) retinol; and
(B) a salt formed by 2-dimethylaminoethanol and a dermatologically active acid selected from the group consisting of lactic acid, glycolic acid, malic acid, tartaric acid, pyruvic acid, citric acid, salicylic acid, and ascorbic acid; wherein said composition has a pH of from about 5 to about 6 and wherein said retinol and said acid are stable and active upon application to the skin.

13. A composition as defined in claim 12, wherein said dermatologically active acid is ascorbic acid.

14. A composition as defined in claim 12, wherein said dermatologically active acid is glycolic acid.

15. A composition as defined in claim 12, wherein said dermatologically active acid is salicylic acid.

16. A composition as defined in claim 12, wherein said retinol comprises from about 0.01 to about 10 percent by weight, based upon 100 percent by weight of total composition.

17. A composition as defined in claim 16, wherein the amount of said salt ranges from about 0.1 to about 20 percent by weight, based upon 100 percent by weight of total composition.

18. A composition as defined in claim 14, said composition comprises from about 0.01 to about 10 percent by weight of retinol and from about 0.1 to about 20 percent by weight of said salt, based upon 100 percent of total composition.

19. A composition as defined in claim 15, said composition comprises from about 0.01 to about 10 percent by weight of retinol and from about 0.1 to about 20 percent by weight of said salt, based upon 100 percent of total composition.

20. A composition as defined in claim 12, further comprising (C) at least one second neutralized salt, other than N,N-dimethylethanolammonium salt, of a dermatologically active acid.

21. A composition as defined in claim 20, wherein said second neutralized salt is a salt of an alkali hydroxide, alkanolamine, amino acid, or any combination of any of the foregoing.

22. A composition as defined in claim 20, wherein said second neutralized salt is a salt of sodium hydroxide, potassium hydroxide, diethanolamine, triethanolamine, aminobutanol, arginine, lysine, or any combination of any of the foregoing.

* * * * *